United States Patent [19]
Glenn, Jr. et al.

[11] Patent Number: 6,028,043
[45] Date of Patent: *Feb. 22, 2000

[54] LIQUID PERSONAL CLEANSING COMPOSITIONS WHICH CONTAIN A COMPLEX COASCERVATE FOR IMPROVED SENSORY PERCEPTION

[75] Inventors: Robert Wayne Glenn, Jr., Maineville; Mark Richard Sine, Morrow; Mark David Evans, Springfield Township; Mary Elizabeth Carethers, West Chester; Sarah Christine Heilshorn, Defiance, all of Ohio

[73] Assignee: The Procter & Gamble Company, Cincinnati, Ohio

[*] Notice: This patent is subject to a terminal disclaimer.

[21] Appl. No.: 09/193,539

[22] Filed: Nov. 17, 1998

Related U.S. Application Data

[63] Continuation of application No. 08/710,830, Sep. 23, 1996, Pat. No. 5,858,938.

[51] Int. Cl.⁷ .......................................................... C11D 3/37
[52] U.S. Cl. .......................... 510/159; 510/418; 510/441; 510/475
[58] Field of Search ..................................... 510/159, 418, 510/441, 475

[56] References Cited

U.S. PATENT DOCUMENTS

| | | | |
|---|---|---|---|
| 4,777,089 | 10/1988 | Takizawa et al. | 428/402.22 |
| 5,089,269 | 2/1992 | Noda et al. | 424/456 |
| 5,716,920 | 2/1998 | Glenn, Jr. et al. | 510/159 |
| 5,759,969 | 6/1998 | Tsaur et al. | 510/158 |
| 5,854,293 | 12/1998 | Glenn, Jr. | 514/844 |
| 5,858,938 | 1/1999 | Glenn, Jr. et al. | 510/130 |

FOREIGN PATENT DOCUMENTS

| | | |
|---|---|---|
| 273823 A1 | 7/1988 | European Pat. Off. . |
| 96/20612 | 7/1996 | WIPO . |

*Primary Examiner*—Yogendra Gupta
*Assistant Examiner*—John R. Hardee
*Attorney, Agent, or Firm*—Tara M. Rosnell; Darryl C. Little; Fumiko Tsuneki

[57] ABSTRACT

Liquid personal cleansing compositions which comprise a complex coascervate, a lipophilic skin moisturizing agent, a stabilizer, a lathering surfactant and water are disclosed. The complex coascervate comprises particles having a particle size distribution such that at least about 10% by weight of the particles have a diameter of at least about 20 microns. The particles comprising the complex coascervate comprise 1) a polycation having a minimum filtrate with of about 10 grams, and 2) a polyanion. The complex coascervate is essentially free of cross-linking agent.

19 Claims, No Drawings

LIQUID PERSONAL CLEANSING COMPOSITIONS WHICH CONTAIN A COMPLEX COACERVATE FOR IMPROVED SENSORY PERCEPTION

A continuation of Ser. No. 08/710,830, filed Sep. 23, 1996, now U.S. Pat. No. 5,858,938.

TECHNICAL FIELD

The present invention relates to liquid personal cleansing emulsions compositions which provide moisturization to the skin and which exhibit desirable skin feel characteristics. The liquid personal cleansing compositions of the present invention contain a complex coacervate comprising relatively large particles which deposits on the skin and provides desirable skin feel characteristics for the composition.

BACKGROUND OF THE INVENTION

Liquid personal cleansing products are becoming more popular in the United States and around the world. Desirable liquid personal cleansing compositions must meet a number of criteria. For example, in order to be acceptable to consumers, a liquid personal cleansing product must exhibit good cleaning properties, must exhibit good lathering characteristics, must be mild to the skin (not cause drying or irritation) and preferably should even provide a moisturization benefit to the skin.

Liquid personal cleansing products which contain high levels of lipophilic skin conditioning agents have been disclosed. In fact, consumer products, such as Olay Moisturizing Body Wash, which, especially when used with the Olay Cleansing Puff, deposit lipophilic skin conditioning agents on the skin are enormously popular with consumers. Nevertheless, some consumers dislike the skin feel that can result from compositions which deposit large amounts of lipophilic ingredients to the skin. Some consumers describe the lipophilic residues on their skin as "greasy", or "tacky". Therefore, it would be desirable to provide a liquid personal cleansing composition which provide a moisturizing benefit to the skin, but which do not cause the skin to feel greasy or tacky.

It has now been found that liquid personal cleansing compositions which contain lipophilic skin moisturizing agents, but which also contain a complex coacervate comprised of relatively large particles, will provide a moisturization benefit, but will not leave the skin feeling greasy or tacky.

SUMMARY OF THE INVENTION

The present invention relates to liquid personal cleansing emulsion compositions which comprise from about 0.05 to about 5% of a complex coacervate, from about 1% to about 30% of a lipophilic skin moisturizing agent, from about 0.1% to about 10% of a stabilizer, from about 5% to about 30% of a lathering surfactant and water. The particles comprising the complex coacervate comprise 1) a polycation having a minimum filtrate weight of about 10 grams and 2) a polyanion.

DETAILED DESCRIPTION OF THE INVENTION

The present invention relates to liquid personal cleansing emulsion compositions which provide moisturization to the skin and which exhibit desirable skin feel characteristics. As used herein, "liquid personal cleansing compositions" refers to rinse off personal cleansing compositions including, but not limited to, shower washes, liquid handsoaps, and shampoos. The liquid personal cleansing compositions of the present invention are emulsions which contain a moisturizing phase comprising a lipophilic skin moisturizing agent and an aqueous cleansing phase comprising a complex coacervate, a surfactant, a stabilizer and water. The complex coacervate comprises particles having a particle size distribution such that at least about 10% by weight of the particles have a diameter of greater than about 20 microns. For purposes of the present invention, the diameter of a particle means the longest length of that particle. It has been found that when these large-particle size complex coacervate particles are employed in the compositions herein, that the sticky rinse feel which can otherwise result from the inclusion of the lipophilic skin moisturizing agent is avoided or minimized.

These liquid personal cleansing emulsion compositions have a viscosity ranging from about 2,000 centipoise to about 100,000 centipoise, preferably from about 5,000 centipoise to about 70,000 centipoise, more preferably from about 10,000 centipoise to about 40,000 centipoise and a yield point ranging from about 5 to about 90 dynes/sq. cm., preferably from about 7 to about 50 dynes/sq. cm., more preferably from about 9 to about 40 dynes/sq. cm. and most preferably from about 11 to about 30 dynes/sq. cm. The personal cleansing compositions of the present invention, including the ingredients comprising them and a process for making them are described in detail as follows:

I. The Ingredients

A. The Complex Coacervate

The personal cleansing compositions of the present invention comprise a complex coacervate which comprises particles which have a particle size distribution such that at least about 10%, preferably at least about 20%, more preferably at least about 30%, even more preferably at least about 50% and most preferably at least about 80% by weight of the particles have a diameter of greater than about 20 microns, preferably greater than about 50 microns, more preferably greater than about 100 microns, even more preferably greater than about 200 microns, and most preferably greater than about 500 microns. It has been found that when at least about 10% by weight of the droplets comprising the complex coacervate have a diameter of greater than about 20 microns, that the coacervate will deposit on the skin and provide desirable skin feel characteristics for the liquid personal cleansing composition.

The complex coacervate particles comprise 1) a polycation having a minimum filtrate weight of at least about 10 grams, and 2) a polyanion. The complex coacervate particles typically comprise from about 0.1% to about 15%, preferably from about 0.5% to about 10%, more preferably from about 1% to about 5% polycation and from about 0.01% to about 10%, preferably from about 0.05% to about 5%, more preferably from about 0.1% to about 1% of polyanion. The ratio of polycation to the polyanion in the complex coacervate particles ranges from about 30:1 to about 1:5, preferably from about 20:1 to about 1:2, more preferably from about 15:1 to about 1:1.

Polycations which are suitable for use in the complex coacervate described herein have a minimum filtrate weight of about 10 grams, preferably about 15 grams, more preferably about 20 grams, as measured by the Filtrate Weight Method set forth hereinafter in the Analytical Methods Section. Polycations having a filtrate weight of less than about 10 grams will not necessarily be capable of forming a coacervate.

Proteins having a average molecular weight ranging from about 50 to about 1,000,000 are preferred polycations for use in the present invention. Preferred proteins for use herein include, for example, gelatin, ovalbumin, serum albumin, casein, chitin, and mixtures thereof.

Gelatin is an especially preferred protein for use as a polycation in the present invention. Gelatins can be characterized according to bloom strength. Bloom strength is the force (measured in grammes) required to depress the surface of a 6 3/3% w/w gel, matured at 10° C. for 16–18 hours, a distance of 4 mm using a flat-bottomed plunger 12.7 mm in diameter. The instrument used is the Bloom Gelometer. A semi-automated version, the Bloom Electronic Jelly Tester, can also be used Gelatins having a bloom strength ranging from about 60 to about 300, preferably from about 75 to about 300, more preferably from about 100 to about 300 and most preferably from about 150 to about 300 are suitable for use herein.

Other polycations having the requisite filtrate weight, such as polyvinylamine and cellulose derivatives, may also suitably be employed for use herein.

The polyanions suitable for use in the complex coacervates described herein includes, for example, polyphosphate, gum arabic, sodium alginate, carrageenan, cellulose acetate, phthalate, pectin, carboxymethylcellulose, ethylene maleic anhydride, and mixtures thereof.

Polyphosphate is an especially preferred polyanion for use herein.

The liquid personal cleansing compositions herein comprise from about 0.05% to about 5%, preferably from about 0.1% to about 3%, more preferably from about 0.3% to about 2% of the complex coacervate.

The complex coacervate particles are prepared by preparing a solution containing the polycation and the polyanion, lowering the pH of the solution to less than about 5.0 (only when the polycation is gelatin), allowing the coacervate to form, and then cooling the solution. The complex coacervate may be formed and then added to the personal cleansing compositions herein, or the polycation and polyanion can be added to the personal cleansing composition and the complex coacervate formed in situ.

In order to deposit efficiently on the skin, it is preferred that the complex coacervate has a hardness ranging from about 10 to about 1400 grams force, preferably from about 50 to about 1200 grams force, more preferably from about 100 to about 1000 grams force, as measured by the Strength of Coacervate Method set forth hereinafter in the Analytical Methods Section. Complex coacervate which has a hardness of greater than about 1400 grams force will not deposit efficiently on the skin and will not, therefore, provide the skin feel benefits taught herein.

It is preferred that the mixture of polycation and polyanion be essentially free of cross-linking agent in order to ensure that the complex coacervate particles have the requisite hardness characteristics to allow them to deposit on the skin. When substantial amounts of a cross linking agent are employed herein, the complex coacervate particles will be too hard to deposit on the skin. As used herein "essentially free of cross-linking agent" means that the mixture contains less than about 0.25% of cross-linking agent. Cross-linking agents are elements, groups or compounds which bridge together two chains of polymer molecules by joining certain carbon atoms of the chains by primary chemical bonds. Cross-linking agents include for example, gluteraldehyde, urea, formaldehyde, phenol, tannic acid, and mixtures thereof.

The particle size of the complex coacervate particles is a function of the RPM of the mixer, the composition of the aqueous solution and the rheology of the aqueous solution. In general, the lower the RPM of the mixer, the larger the particle size of the complex coacervate particles.

B. The Lipophilic Skin Moisturizing Agent

A lipid skin moisturizing agent is employed in the personal cleansing compositions herein. The lipid skin moisturizing agent provides a moisturizing benefit to the user of the personal cleansing product when the lipid moisturizing agent is deposited to the user's skin.

Two types of rheological parameters are used to define the lipophilic skin moisturizing agent used herein. The viscosity of the lipophilic skin moisturizing agent is represented by consistency (k) and shear index (n). The lipophilic skin moisturizing agents for use herein typically have a consistency (k) ranging from about 5 to about 5,000 poise, preferably from about 10 to about 3,000 poise, more preferably from about 50 to about 2,000 poise, as measured by the Consistency (k) Method hereinafter set forth in the Analytical Methods section. Suitable lipophilic skin moisturizing agents for use herein further have a shear index (n) ranging from about 0.01 to about 0.9, preferably from about 0.1 to about 0.5, more preferably from about 0.2 to about 0.5, as measured by the Shear Insex Method hereinafter set forth in the Analytical methods section.

While not being bound by any theory, it is believed that lipophilic skin moisturizing agents having rheology properties other than those defined herein are either too easily emulsified and hence will not deposit, or are too "stiff" to adhere or deposit on to skin and provide a moisturization benefit. In addition, the rheological properties of the lipophilic skin moisturizing agent are also important to user perception. Some lipophilic skin moisturizing agents, on deposition to the skin, are considered too sticky and are not preferred by the user.

In some cases, the lipophilic skin moisturizing agent can also desirably be defined in terms of its solubility parameter, as defined by *Vaughan in Cosmetics and Toiletries*, Vol. 103, p. 47–69, October 1988. A lipophilic skin moisturizing agent having a Vaughan solubility Parameter (VSP) of from 5 to 10, preferably from 5.5 to 9 is suitable for use in the liquid personal cleansing compositions herein.

A wide variety of lipid type materials and mixtures of materials are suitable for use as the lipophilic skin moisturizing agents in the personal cleansing compositions of the present invention. Preferably, the lipophilic skin conditioning agent is selected from the group consisting of hydrocarbon oils and waxes, silicones, fatty acid derivatives, cholesterol, cholesterol derivatives, di and tri-glycerides, vegetable oils, vegetable oil derivatives, liquid nondigestible oils such as those described in U.S. Pat. No. 3,600,186 to Mattson; Issued Aug. 17, 1971 and U.S. Pat. Nos. 4,005,195 and 4,005,196 to Jandacek et al; both issued Jan. 25, 1977, all of which are herein incorporated by reference, or blends of liquid digestible or nondigestible oils with solid polyol polyesters such as those described in U.S. Pat. No. 4,797,300 to Jandacek; issued Jan. 10, 1989; U.S Pat. Nos. 5,306,514, 5,306,516 and 5,306,515 to Letton; all issued Apr. 26, 1994, all of which are herein incorporated by reference, and acetoglyceride esters, alkyl esters, alkenyl esters, lanolin and its derivatives, milk -tri- glycerides, wax esters, beeswax derivatives, sterols, phospholipids and mixtures thereof. Fatty acids, fatty acid soaps and water soluble polyols are specifically excluded from our definition of a lipophilic skin moisturizing agent.

Hydrocarbon oils and waxes: Some examples are petrolatum, mineral oil micro-crystalline waxes, polyalkenes (e.g. hydrogenated and nonhydrogenated polybutene and polydecene), paraffins, cerasin, ozokerite, polyethylene and perhydrosqualene. Blends of petrolatum and hydrogenated and nonhydrogenated high molecular weight polybutenes wherein the ratio of petrolatum to polybutene ranges from about 90:10 to about 40:60 are also suitable for use as the lipid skin moisturizing agent in the compositions herein.

Silicone Oils: Some examples are dimethicone copolyol, dimethylpolysiloxane, diethylpolysiloxane, high molecular weight dimethicone, mixed C1–C30 alkyl polysiloxane, phenyl dimethicone, dimethiconol, and mixtures thereof. More preferred are non-volatile silicones selected from dimethicone, dimethiconol, mixed C1–C30 alkyl polysiloxane, and mixtures thereof. Nonlimiting examples of silicones useful herein are described in U.S. Pat. No. 5,011,681, to Ciotti et al., issued Apr. 30, 1991, which is incorporated by reference.

Di and tri-glycerides: Some examples are castor oil, soy bean oil, derivatized soybean oils such as maleated soy bean oil, safflower oil, cotton seed oil, corn oil, walnut oil, peanut oil, olive oil, cod liver oil, almond oil, avocado oil, palm oil and sesame oil, vegetable oils and vegetable oil derivatives; coconut oil and derivatized coconut oil, cottonseed oil and derivatized cottonseed oil, jojoba oil, cocoa butter, and the like.

Acetoplyceride esters are used and an example is acetylated monoglycerides.

Lanolin and its derivatives are preferred and some examples are lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate.

It is most preferred when at least 75% of the lipophilic skin conditioning agent is comprised of lipids selected from the group consisting: petrolatum, blends of petrolatum and high molecular weight polybutene, mineral oil, liquid nondigestible oils (e.g. liquid cottonseed sucrose octaesters) or blends of liquid digestible or nondigestible oils with solid polyol polyesters (e.g. sucrose octaesters prepared from C22 fatty acids) wherein the ratio of liquid digestible or nondigestible oil to solid polyol polyester ranges from about 96:4 to about 80:20, hydrogenated or nonhydrogenated polybutene, micro-crystalline wax, polyalkene, paraffin, cerasin, ozokerite, polyethylene, perhydrosqualene; dimethicones, alkyl siloxane, polymethylsiloxane, methylphenylpolysiloxane and mixtures thereof. When as blend of petrolatum and other lipids is used, the ratio of petrolatum to the other selected lipids (hydrogenated or unhydrogenated polybutene or polydecene or mineral oil) is preferably from about 10:1 to about 1:2, more preferably from about 5:1 to about 1:1.

C. The Stabilizer

The liquid personal cleansing compositions of the present invention also typically contain from about 0.1% to about 10%, preferably from about 0.25% to about 8%, more preferably from about 0.5% to about 5% of a stabilizer.

The stabilizer is used to form a crystalline stabilizing network in the emulsion that prevents the lipophilic skin moisturizer agent droplets from coalescing and phase splitting in the product. The network exhibits time dependent recovery of viscosity after shearing (e.g., thixotropy).

The stabilizers used herein are not surfactants. The stabilizers provide improved shelf and stress stability, but allow the oil-in-water emulsion to separate upon lathering, and thereby provide for increased deposition of the lipophilic skin moisturizing agent onto the skin. This is particularly true when the oil-in-water cleansing emulsions of the present invention are used in conjunction with a polymeric diamond meshed sponge implement such as that described in Campagnoli; U.S. Pat. No. 5,144,744; Issued Sep. 8, 1992, herein incorporated by reference.

In one embodiment of the present invention, the stabilizer employed in the personal cleansing compositions herein comprises a crystalline, hydroxyl-containing stabilizer. This stabilizer can be a hydroxyl-containing fatty acid, fatty ester or fatty soap water-insoluble wax-like substance or the like.

The crystalline, hydroxy-containing stabilizer is selected from the group consisting of:

(i)

$$\begin{array}{l} CH_2\!\!-\!\!OR_1 \\ |\\ CH\!\!-\!\!OR_2 \\ |\\ CH_2\!\!-\!\!OR_3 \end{array}$$

wherein

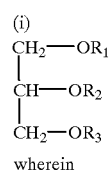

$R_1$ is $-\!\!\overset{\overset{\displaystyle O}{\|}}{C}\!\!-\!\!R_4(CHOH)_xR_5(CHOH)_yR_6;$ $R_2$ is $R_1$ or H
$R_3$ is $R_1$ or H
$R_4$ is $C_{0-20}$ Alykl
$R_5$ is $C_{0-20}$ Alykl,
$R_6$ is $C_{0-20}$ Alykl
$R_4 + R_5 + R_6 = C_{10-22}$
and wherein $1 \leq x + y \leq 4$;

(ii)

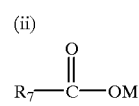

$R_7\!\!-\!\!\overset{\overset{\displaystyle O}{\|}}{C}\!\!-\!\!OM$ wherein
$R_7$ is $-\!\!R_4(CHOH)_xR_5(CHOH)_yR_6$
M is $Na^+$, $K^+$ or $Mg^{++}$, or H; and -continued iii) mixtures thereof;

Some preferred hydroxyl-containing stabilizers include 12-hydroxystearic acid, 9,10-dihydroxystearic acid, tri-9, 10-dihydroxystearin and tri- 12-hydroxystearin (hydrogenated castor oil is mostly tri-12-hydroxystearin). Tri-12-hydroxystearin is most preferred for use in the emulsion compositions herein.

When these crystalline, hydroxyl-containing stabilizers are utilized in the personal cleansing compositions herein, they are typically present at from about 0.5% to 10%, preferably from 0.75% to 8%, more preferably from 1.25% to about 5% of the liquid personal cleansing compositions. The stabilizer is insoluble in water under ambient to near ambient conditions.

Alternatively, the stabilizer employed in the personal cleansing compositions herein can comprise a polymeric thickener. When polymeric thickeners as the stabilizer in the personal cleansing compositions herein, they are typically included in an amount ranging from about 0.01% to about 5%, preferably from about 0.3% to about 3%, by weight of the composition. The polymeric thickener is preferably an anionic, nonionic, cationic or hydrophobically modifier polymer selected from the group consisting of cationic polysaccharides of the cationic guar gum class with molecular weights of 1,000 to 3,000,000, anionic cationic and nonionic homopolymers derived from acrylic and/or methacrylic acid, anionic cationic and nonionic cellulose resins, cationic copolymers of dimethyldialkylammonium chloride and acrylic acid, cationic homopolymers of dimethylalkylammonium chloride, cationic polyalkylene and ethoxypolyalkylene imines, polyethylene glycol of molecular weight from 100,000 to 4,000,000, and mixtures thereof. Preferably, the polymer is selected from the group consisting of Sodium Polyacrylate, hydroxy ethyl Cellulose, Cetyl Hydroxy Ethyl Cellulose, and Polyquaternium 10.

Alternatively, the stabilizer employed in the personal cleansing compositions herein can comprise C10–C22 ethylene glycol fatty acid esters. C10–C22 ethylene glycol fatty acid esters can also be desirably employed in combination with the polymeric thickeners hereinbefore described. The ester is preferably a diester, more preferably a C14–C18 diester, most preferably ethylene glycol distearate. When C10–C22 ethylene glycol fatty acid esters are utilized as the stabilizer in the personal cleansing compositions herein, they are typically present at from about 3% to about 10%, preferably from about 5% to about 8%, more preferably from about 6% to about 8% of the personal cleansing compositions.

Another class of stabilizer which can be employed in the personal cleansing compositions of the present invention comprises dispersed amorphous silica selected from the group consisting of fumed silica and precipitated silica and mixtures thereof. As used herein the term "dispersed amorphous silica" refers to small, finely divided non-crystalline silica having a mean agglomerate particle size of less than about 100 microns.

Fumed silica, which is also known as arced silica, is produced by the vapor phase hydrolysis of silicon tetrachloride in a hydrogen oxygen flame. It is believed that the combustion process creates silicone dioxide molecules which condense to form particles. The particles collide, attach and sinter together. The result of this process is a three dimensional branched chain aggregate. Once the aggregate cools below the fusion point of silica, which is about 1710° C., further collisions result in mechanical entanglement of the chains to form agglomerates. Precipitated silicas and silica gels are generally made in aqueous solution. See, Cabot Technical Data Pamphlet TD-100 entitled "CAB-O-SIL® Untreated Fumed Silica Properties and Functions", October 1993, and Cabot Technical Dat Pamphlet TD-104 entitled "CAB-O-SIL® Fumed Silica in Cosmetic and Personal Care Products", March 1992, both of which are herein incorporated by reference.

The firmed silica preferably has a mean agglomerate particle size ranging from about 0.1 microns to about 100 microns, preferably from about 1 micron to about 50 microns, and more preferably from about 10 microns to about 30 microns. The agglomerates are composed of aggregates which have a mean particle size ranging from about 0.01 microns to about 15 microns, preferably from about 0.05 microns to about 10 microns, more preferably from about 0.1 microns to about 5 microns and most preferably from about 0.2 microns to about 0.3 microns. The silica preferably has a surface area greater than 50 sq. m/gram, more preferably greater than about 130 sq. m./gram, most preferably greater than about 180 sq. m./gram.

When amorphous silicas are used as the stabilizer herein, they are typically included in the emulsion compositions at levels ranging from about 0.1% to about 10%, preferably from about 0.25% to about 8%, more preferably from about 0.5% to about 5%.

A fourth class of stabilizer which can be employed in the personal cleansing compositions of the present invention comprises dispersed smectite clay selected from the group consisting of bentonite and hectorite and mixtures thereof. Bentonite is a colloidal aluminum clay sulfate. See Merck Index, Eleventh Edition, 1989, entry 1062, p. 164, which is incorporated by reference. Hectorite is a clay containing sodium, magnesium, lithium, silicon, oxygen, hydrogen and flourine. See Merck Index, eleventh Edition, 1989, entry 4538, p. 729, which is herein incorporated by reference.

When smectite clay is employed as the stabilizer in the personal cleansing compositions of the present invention, it is typically included in amounts ranging from about 0.1% to about 10%, preferably from about 0.25% to about 8%, more preferably from about 0.5% to about 5%.

D. The Lathering Surfactant

The personal cleansing compositions of the present invention also comprises a lathering surfactant selected from the group consisting of anionic surfactants; nonionic surfactants, cationic surfactants, amphoteric surfactants, and mixtures thereof.

The lathering surfactant is defined herein as a surfactant or surfactant mixture thereof that when combined have an equilibrium surface tension of between 15 and 50 dynes/cm, more preferably between 25 and 40 dynes/cm as measured at the CMC (critical micelle concentration) at 25° C. Some surfactant mixes can have a surface tension lower than those of its individual components.

The personal cleansing compositions herein comprise from about 5% to about 30%, preferably from about 5% to about 25%, and most preferably from about 10% to about 25% of a lathering surfactant.

Anionic surfactants useful herein include: acyl isethionates, acyl sarcosinates, alkylglycerylether sulfonates, alkyl sulfates, alkyl sulfates, acyl lactylate, methylacyl taurates, paraffin sulfonates, linear alkyl benzene sulfonates, N-acyl glutamates, alkyl sulfosuccinates, alpha sulfo fatty acid esters, alkyl ether carboxylates, alkyl phosphate esters, ethoxylated alkyl phosphate esters, alpha olefin sulphates, the alkyl ether sulfates (with 1 to 12 ethoxy groups) and mixtures thereof, wherein said surfactants contain C8 to C22 alkyl chains and wherein the counterion is selected from the group consisting of: Na, K, $NH_4$, $N(CH_2CH_2OH)_3$. The anionic surfactant is more preferred when selected from the group consisting of acyl isethionate, acyl sarcosinates, acyl lactylates, alkyl sulfosuccinates, alkylglycerylether sulfonates, methylacyl taurates, alkyl ether sulfates, alkyl sulfates, alkyl phosphate esters and mixtures thereof, wherein said surfactants contain has C8 to C14 alkyl chains and is present at a level of from about 8% to about 20%.

Amphoteric synthetic surfactants cannot serve as the sole surfactant in this product, but are preferred as a co-surfactant at a lower level of from about 1% to about 10%, by weight and the more preferred types are selected from alkyl-ampho mono- and di-acetates, alkyl betaines, alkyl dimethyl amine oxides, alkyl sultaines, alkyl amidopropyl betaines, alkyl amidopropyl hydroxysultaines, and mixtures thereof, wherein said surfactants contain C8 to C22 alkyl chains.

Nonionic synthetic surfactant cannot serve as the sole surfactant in this product, but can be used as a co-surfactant at a lower level of from about 1% to about 15% by weight. The more preferred types selected from the group consisting: alkyl glucose amides, alkyl glucose esters, polyoxyethylene amides, fatty alkane amides, alkyl amine oxides, alkyl polyglucosides, polyoxy ethylene alkyl phenols, polyoxyethylene esters of fatty acids, EO/PO block co-polymers such as polyoxamines and poloxamers, sorbitan esters and alcohol esters, and mixtures thereof.

Cationic synthetic surfactant cannot serve as the sole surfactant in this product, but are preferred as a co-surfactant at a lower level of from about 0.5% to about 6%, by weight. The more preferred types of cationic surfactants are selected from the group consisting of: alkyl trimonium chloride and methosulfate, and dialkyldimonium chloride and methyl sulphate, and alkyl alkonium chloride and methyl sulphate and mixtures thereof. These surfactants contain C12 to C24 carbon atoms per alkyl chain. The most preferred cationic is selected from the group consisting of stearalkonium chloride, stearyltrimonium chloride, Di-stearyl-dimonium chloride, and mixtures thereof. Cationic surfactants may also act as a lipid deposition aid.

The liquid emulsions compositions herein can also optionally contain C8–C14 fatty acid soap; where the soap has a counterion selected from the group consisting of K and $N(CH2CH2OH)_3$, and mixtures thereof, in addition to the lathering synthetic surfactant. In one preferred embodiment of the present invention, the liquid personal cleansing compositions contain less than about 5%, preferably less than about 4%, more preferably less than about 3% and most preferably less than about 2% by weight of the composition of fatty acid soap.

E. Water

The moisturizing personal cleansing compositions of the present invention comprise water as an essential component. The water is typically present at a level of from about 30% to about 80%, preferably from about 40% to about 75%, and most preferably from about 40% to about 65% of the personal cleansing compositions of the present invention.

F. Optional Ingredients

The personal cleansing compositions of the present invention can also contain a number of optional ingredients.

For example, the liquid personal cleansing compositions of the present invention can optionally include water-dispersible, gel-forming polymers. This polymer is preferably a anionic, nonionic, cationic or hydrophobically modified polymer, selected from the group consisting of cationic polysaccharides of the cationic guar gum class with molecular weights of 1,000 to 3,000,000, anionic, cationic and nonionic homopolymers derived from acrylic and/or methacrylic acid, anionic, cationic and nonionic cellulose resins; cationic copolymers of dimethyldialkylammonium chloride and acrylic acid; cationic homopolymers of dimethyldialkylammonium chloride; cationic polyalkylene and ethoxypolyalkylene imines polyethylene glycol of molecular weight from 100,00 to 4,000,000; and mixtures thereof. Preferably, the polymer is selected form the group consisting of Sodium Polyacrylate, Hydroxy Ethyl Cellulose, Cetyl Hydroxy Ethyl Cellulose, and Polyquaternium 10.

The polymer is preferably included in the compositions of the present invention at a level of from about 0.1 parts to 1 part, more preferably 0.1 parts to 0.5 parts. The polymers can improve the sensory feel of the lipid on skin in addition to providing product stabilization. The improved sensory feel results from reduced tackiness and greasiness and improved smoothness. It is an especially preferred embodiment to use mixture of polymers, some of which are preferred for product stabilization, some are preferred for improved sensory feel. Preferred polymers to improve sensory feel are selected from the group consisting: of polyethylene glycol, hydroxypropyl guar, guar hydroxypropyltrimonium chloride, polyquatemary 3, 5, 6, 7, 10, 11 and 24 and mixtures thereof.

Another highly preferred optional component of the present compositions are one or more humectants and solutes. A variety of humectants and solutes can be employed and can be present at a level of from about 0.5 % to about 25%, more preferably from about 3.0% to about 20%. The humectants and solutes are non-volatile, organic materials having a solubility of a least 5% in 10% water. A preferred water soluble, organic material is selected from the group consisting of a polyol of the structure:

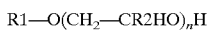

where R1=H, C1–C4 alkyl; R2=H, $CH_3$ and n=1–200; C2–C10 alkane diols; guanidine; glycolic acid and glycolate salts (e.g. ammonium and quaternary alkyl ammonium); lactic acid and lactate salts (e.g. ammonium and quaternary alkyl ammonium); polyhydroxy alcohols such as sorbitol, glycerol, hexanetriol, propylene glycol, hexylene glycol and the like; polyethylene glycol; sugars and starches; sugar and starch derivatives (e.g. alkoxylated glucose); panthenol (including D-, L-, and the D,L- forms); pyrrolidone carboxylic acid; hyaluronic acid; lactamide monoethanolamine; acetamide monoethanolamine; urea; and ethanol amines of the general structure $(HOCH_2CH_2)_xNH_y$, where $x=1-3$; $y=0-2$, and $x+y=3$, and mixtures thereof. The most preferred polyols are selected from the group consisting of glycerine, polyoxypropylene(1) glycerol and polyoxypropylene(3) glycerol, sorbitol, butylene glycol, propylene glycol, sucrose, urea and triethanol amine.

Preferred water soluble organic material are selected from the group consisting of glycerine, polyoxypropylene (1) glycerol and polyoxypropylene (3) glycerol, sorbitol, butylene glycol, propylene glycol, sucrose, and urea and triethanolamine.

The use of oil thickening polymers, such as those listed in EP 0 547 897 A2 to Hewitt, published Jun. 23, 1993, incorporated herein by reference, can also be included in the water phase of the emulsions of the present invention.

A variety of additional ingredients can be incorporated into the compositions of the present invention. These materials including, but not limited to, liquid appearance aids, salts and their hydrates and other "filler materials" are listed in U.S. Pat. No. 5,340,492, to Kacher et al., issued Aug. 23, 1994, and U.S. Pat. No. 4,919,934, to Deckner et al., issued Apr. 24, 1990; which is incorporated herein by reference.

Other non limiting examples of these additional ingredients include vitamins and derivatives thereof (e.g., ascorbic acid, vitamin E, tocopheryl acetate, and the like); sunscreens; thickening agents (e.g., polyol alkoxy ester, available as Crothix from Croda at levels up to 2% and xanthan gum at levels up to about 2%); preservatives for maintaining the anti microbial integrity of the compositions; anti-acne medicaments (resorcinol, salicylic acid, and the like); antioxidants; skin soothing and healing agents such as aloe vera extract, allantoin and the like; chelators and sequestrants; and agents suitable for aesthetic purposes such as fragrances, essential oils, skin sensates, pigments, pearlescent agents (e.g., mica and titanium dioxide), additives to impart a draggy rinse feel (e.g., fumed silica), additives to enhance deposition (e.g., maleated soybean oil at levels up to 3%), lakes, colorings, and the like (e.g., clove oil, menthol, camphor, eucalyptus oil, and eugenol).

II. Process for Preparing the Liquid Personal Cleansing Compositions Herein

The liquid personal cleansing compositions of the present invention can be made according to standard processes for preparing liquid personal cleansing compositions which contain both a moisturizing phase and a cleansing phase.

Analytical Methods

A number of parameters used to characterize elements of the present invention are quantified by particular experimental analytical procedures. Each of these procedures are described in detail as follows:

1. Consistency (k) and Shear Index (n) of the Lipophilic Skin Moisturizing Agent The Carrimed CSL 100 Controlled Stress Rheometer is used to determine Shear Index, n, and Consistency, k, of the lipophilic skin moisturizing agent used herein. The determination is performed at 35° C. with the 4 cm 2° cone measuring system typically set with a 51 micron gap and is performed via the programmed application of a shear stress (typically from about 0.06 dynes/sq. cm to about 5,000 dynes/sq. cm) over time. If this stress results in a deformation of the sample, i.e. strain of the measuring geometry of at least 10–4 rad/sec, then this rate of strain is reported as a shear rate. These data are used to create a viscosity $\mu$ Vs. shear rate $\gamma'$ flow curve for the material. This flow curve can then be modeled in order to provide a mathematical expression that describes the material's behavior within specific limits of shear stress and shear rate. These results were fitted with the following well accepted power law model (see for instance: *Chemical Engineering*, by Coulson and Richardson, Pergamon, 1982 or *Transport Phenomena* by Bird, Stewart and Lightfoot, Wiley, 1960):

$$\text{Viscosity}, \mu = k(\gamma')^{n-1}$$

2. Viscosity of the Liquid Personal Cleansing Composition

The Wells-Brookfield Cone/Plate Model DV-II+ Viscometer is used to determine the viscosity of the liquid personal cleansing compositions herein. The determination is performed at 25° C. with the 2.4 cm° cone (Spindle CP-41) measuring system with a gap of 0.013 mm between the two small pins on the respective cone and plate. The measurement is performed by injecting 0.5 ml of the sample to be analyzed between the cone and plate and toating the cone at a set speed of 1 rpm. The resistance to the rotation of the one produces a torque that is proportional to the shear stress of the liquid sample. The amount of torque is read and computed by the viscometer into absolute centipoise units (mPa*s) based on geometric constants of the cone, the rate of rotation, and the stress related torque.

3. Filtrate Weight of Polycation

The filtrate weight of a polycation is measured via a filtration apparatus which utilizes mechanical suction to effectively filter out the polycation coacervate.

The complex coacervate is formed by mixing together dissolved polycation and dissolved sodium hexametaphosphate (Glass H from FMC Corporation—average $P_2O_5$ chain length of 21. The total amount of combined polycation and hexametaphosphate to be mixed together is 12 grams. The ratio of polycation to hexametaphosphate to be employed is ratio at which a precipitate is formed. When gelatin is the polycation, the ratio of gelatin to hexametaphosphate to be employed is 11:1 (e.g., 11 grams of gelatin and 1 gram of hexametaphosphate).

Once the proper amounts of polycation and hexametaphosphate to be mixed together has been calculated as described above, both the polycation and the hexametaphosphate are dissolved in de-ionized water with heating and stirring. The total amount of water to be used for dissolving the polycation and the hexametaphosphate is 286 grams. The hexametaphosphate is dissolved in 19x by weight water. The polycation is dissolved in the remainder of the water.

After the polycation and the hexametaphosphate have been separately dissolved, the two solutions are mixed together. When gelatin is used as the polycation, the pH is then adjusted to 3.7 with glacial acetic acid added drop-wise while stirring. The resultant mixture is then cooled to room temperature to induce a phase separated coacervate polycation/hexametaphosphate/water complex which can be filtered and weighed. The coacervate complex is filtered from the solution via a setup consisting of a 1000 ml Erlenmeyer Flask, 100 mm porcelain Buchner funnel, and 90 mm medium porosity/medium flow rate Whatman grade No. 40 filter paper. The mechanical suction is provided via a ⅙ horsepower Gast vacuum pump. The filtered coacervate complex is weighed and the weight is reported in grams as the filtrate weight of polycation.

4. Particle Size Distribution for LiPophilic Skin Moisturizing Agent Particles

The particle size distribution of the lipophilic skin moisturizing agent is estimated via a scanning laser microscope which is commercially produced by Lasentec (Lasentec M100F). The lasentec M100F measures suspended particles by scanning a focused laser beam at a constant velocity across particles suspended in the liquid and moving past the window of a probe. When the focal point intercepts a particle, some light is scattered back to the probe and converted to an electronic pulse, which is converted to size by the relationship: d=v*t. The duration of the pulse represents the time (t) the particle is illuminated in the focal point. Because the velocity (v) of the focal spot is known, (d) is therefore the scanned distance across the particle. This distance represents the length of a chord of the particle. The chord length distribution is an accurate direct measure of the particle structure dimensions and particle structure shate as determined on a 3-dimensional basis. The M100 classifies particles into 38 channels, ranging from 1.9 to 1000 microns. The particle size distribution is generated using a length cube weight average chord calculation which gives an estimate of the amount of substance per particle size (versus the number of particles per particle size):

$$\text{Length Cube Weight Average Chord} = \frac{\sum_{i=1}^{k} n_i m_i^4}{\sum_{i=1}^{k} n_i m_i^3}$$

$n_i$=Counts in an individual measurement channel $M_i$=Midpoint of an individual channel k=Upper channel # ($2 \leq k \leq 38$)

The lasentec measures the particle size distribution of everything within the formula including precipitates and air pockets. Therefore, light microscopy is used as a supplemental lipophilic moisturizing agent particle size measurement technique to confirm the data generated by the Lasentec M100F. In this technique, the product is viewed under very low magnification (<10x) between a plate and coverslip and lipophilic moisturizing agent particles sizes are estimated via a micrometer.

5. Yield Point of Liquid Personal Cleansing Compositions

The Carrimed CSL 100 Controlled Stress Rheometer is used to determine the yield point of the liquid personal cleansing compositions. For purposes herein, the yield point is the amount of stress required to produce a strain of 1% on the liquid personal cleansing composition. The determination is performed at 77° F. with the 4 cm 2° cone measuring system set with a 51 micron gap. The determination is performed via the programmed application of a shear stress (typically from about 0.06 dynes/sq. centimeter to about 500 dynes/square centimeter) over time. If this amount of stress results in a deformation of the sample, a shear stress vs. strain curve can be created. From this curve, the yield point of the liquid personal cleansing composition can be calculated.

6. Strength of the Complex Coacervate

A. Preparation

The complex coacervate is formed by combining the formula amounts of the desired polycation and polyanion in aqueous solution. The pH is adjusted to within the range of 3.5 to 4.5 by adding glacial acetic acid drop-wise. The resultant mixture is cooled to induce a phase separated coacervate. The supernatant is decanted, and enough of the complex coacervate is transferred to a petri culture dish (100×15 mm) to completely fill the dish and leave a flat surface flush with the top of the dish. The sample is them allowed to equilibrate at room temperature for 24 hours.

B. Strength Protocol

The Stable MicroSystems Universal TA.XT2 Texture Analyser and the XT.RA Dimension data acquisition system is used to measure the strength of the complex coacervate. The Texture Analyser uses a cylindrical probe (14×11.5 mm) to measure force in compression of the complex coacervate. The probe is set within 2 mm of the top of the complex coacervate sample. The probe pushes down to a trigger force of 5 grams at the speed of 1 mm/sec. this is followed by a 4 mm compression distance at the entrance and exit speeds of 1 mm/sec. The data acquisition system records the required force in compression versus time. The maximum force in compression is recorded as the strength of the complex coacervate.

EXAMPLES

The following shower gel compositions are non-limiting examples of the liquid personal cleansing compositions of the present invention.

| Ingredients | #1 | #2 | #3 | #4 |
|---|---|---|---|---|
| Complex Coacervate Pre-mix Composition: | | | | |
| Gelatin type A; 150 Bloom Strength | 25.32 | 0.0 | 0.0 | 22.07 |
| Gelatin type A, 275 Bloom Strength | 0.00 | 13.83 | 5.10 | 0.00 |
| Hexameta Polyphosphate | 2.94 | 0.38 | 0.46 | 2.94 |
| Glacial Acetic Acid (dropwise to pH <4.4) | ~0.02 | ~0.02 | ~0.02 | ~0.02 |
| De-ionized Water | QS | QS | QS | QS |
| Final Formula with Incorporated Complex Coacervate Premix: | | | | |
| Ammonium Lauryl Sulfate | 3.15 | 3.15 | 2.89 | 3.15 |
| Ammonium Laureth-3 Sulfate | 9.45 | 9.45 | 8.66 | 9.45 |
| Sodium Laroamphoacetate | 5.40 | 5.40 | 4.95 | 5.40 |
| Fatty Acid Soap | 0.0 | 0.0 | 0.0 | 0.0 |
| Trihydroxystearin | 0.75 | 0.75 | 0.75 | 0.75 |
| Complex Coacervate Precipitate Premix | 3.94 | 7.23 | 19.6 | 3.40 |
| Optional Ingredients | 7.48 | 4.14 | 4.14 | 7.78 |
| Petrolatum | 16.50 | 16.50 | 10.00 | 16.50 |
| Water | QS | QS | QS | QS |
| Lather (Ultimate Volume) | 450 | 450 | 450 | 400 |

-continued

| Ingredients | #1 | #2 | #3 | #4 |
|---|---|---|---|---|
| Deposition ($\mu g/cm^2$) | 52 | 19 | | |
| Viscosity (cp) | 13,760 | — | | |
| Yield Point (dynes/cm$^2$) | 9.3 | — | | |

Complex Coacervate Pre-mix Preparation:
1. Dissolve hexameta polyphosphate in 19 times as much water while stirring.
2. Dissolve gelatin in remaining water and heat to 50–60C. while stirring in agitated vessel.
3. Add polyphosphate-water solution to gelatin-water solution.
4. Add glacial acetic acid drop-wise until pH is less than 4.4.
5. Cool Complex Coacervate Mixture while stirring prior to incorporation into formula.

What is claimed is:
1. A liquid personal cleansing composition comprising:
 a) from about 0.05% to about 5% by weight of complex coacervate particles comprising a polycation having a minimum filtrate of about 10 grams and a polyanion, wherein said complex coacervate particles have a hardness ranging from about 10 to about 1400 grams force and wherein said particles have a particle size distribution such that at least about 10% by weight of said particles are greater than about 20 microns;
 b) from about 1% to about 30% by weight of a lipophilic skin moisturizing agent;
 c) from about 0.1 to about 10% by weight of a stabilizer;
 d) from about 5% to about 30% by weight of a lathering surfactant; and
 e) water.

2. A liquid personal cleansing composition according to claim 1 wherein the complex coacervate particles comprise from about 0.1% to about 15% polycation having a minimum filtrate weight of about 10 grams and from about 0.1% to about 10% of a polyanion.

3. A liquid personal cleansing composition according to claim 2 wherein the ratio of the polycation to the polyanion in the complex coacervate particles ranges from about 30:1 to about 1:5.

4. A liquid personal cleansing composition according to claim 3 wherein the lipophilic skin moisturizing agent has a consistency ranging from about 5 to about 5,000 poise and a shear index ranging from about 0.1 to about 0.9.

5. A liquid personal cleansing composition according to claim 4 wherein the polycation comprises gelatin.

6. A liquid personal cleansing composition according to claim 5 wherein the polyanion is selected from the group consisting of polyphosphate, gum arabic, sodium alginate and mixtures thereof.

7. A liquid personal cleansing composition according to claim 6 wherein at least about 50% by weight of the complex coacervate particles have a diameter of greater than about 50 microns.

8. A liquid personal cleansing composition according to claim 6 wherein the stabilizer is a crystalline, hydroxyl-containing stabilizer selected from the group consisting of:

(i)

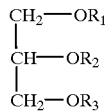

wherein $R_1$ is 

$R_2$ is $R_1$ or H
$R_3$ is $R_1$ or H
$R_4$ is $C_{0-20}$ [Alkyl]Alkylene
$R_5$ is $C_{0-20}$ [Alkyl]Alkylene
$R_6$ is $C_{0-20}$ Alkyl
$R_4 + R_5 + R_6 = C_{10-22}$
and wherein $1 \leq x + y \leq [$, provided $R_4$ and $R_5$ is H when not an alkyl group];

(ii)

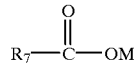

wherein
[$R_7$ is —$R_4(COH)_xR_5(COH)_yR_6$]
$R_7$ is —$R_4(CHOH)_xR_5(CHOH)_7R_6$
M is Na$^+$, K$^+$ or Mg$^{++}$, or H; and
iii) mixtures thereof.

iii) mixtures thereof.

9. A liquid personal cleansing composition according to claim 8 wherein the viscosity of the liquid personal cleansing composition ranges from about 2,000 centipoise to about 100,000 centipoise and a yield point ranging from about 5 to about 90 dynes/sq. cm.

10. A liquid personal cleansing composition according to claim 9 wherein at least 50% by weight of the complex coacervate particles have a diameter of greater than about 100 microns.

11. A liquid personal cleansing composition according to claim 10 wherein the lipophilic skin moisturizing agent comprises petrolatum.

12. A liquid personal cleansing composition comprising:
    a) from about 0.05% to about 5% by weight of complex coacervate particles comprising a polycation having a minimum filtrate weight of about 10 grams and a polyanion, wherein said complex coacervate particles have a particle size distribution such that at least about 10% by weight of the particles have a diameter of greater than about 100 microns, wherein said complex coacervate particles are essentially free of crosslinking agent;
    b) from about 1% to about 30% by weight of a lipophilic skin moisturizng agent;

14. A liquid personal cleansing composition according to claim 13 wherein the ratio of the polycation to the polyanion in the complex coacervate particles ranges from about 30:1 to about 1:5.

15. A liquid personal cleansing composition according to claim 14 wherein the lipophilic skin moisturizing agent has a consistency ranging from about 5 to about 5,000 poise and a shear index ranging from about 0.1 to about 0.9.

16. A liquid personal cleansing composition according to claim 15 wherein the polycation comprises gelatin and wherein the polyanion is selected from the group consisting of polyphosphate, gum arabic, sodium alginate and mixtures thereof.

17. A liquid personal cleansing composition according to claim 16 wherein at least about 50% by weight of the complex coacervate particles have a diameter of greater than about 100 microns.

18. A liquid personal cleansing composition according to claim 17 wherein the stabilizer is a crystalline, hydroxyl-containing stabilizer selected from the group consisting of:

(i)

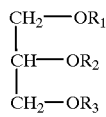

$R_1$ is 

$R_2$ is $R_1$ or H
$R_3$ is $R_1$ or H
$R_4$ is $C_{0-20}$ [Alkyl]<u>Alkylene</u>
$R_5$ is $C_{0-20}$ [Alkyl]<u>Alkylene</u>
$R_6$ is $C_{0-20}$ Alkyl
$R_4 + R_5 + R_6 = C_{10-22}$
and wherein $1 \leq x + y \leq 4$ [, provided $R_4$ and $R_5$ is H when not an alkyl group];
(ii)

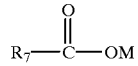

wherein
[$R_7$ is —$R_4(COH)_xR_5(COH)_yR_6$]
$R_7$ is —$R_4(CHOH)_xR_5(CHOH)_yR_6$
M is $Na^+$, $K^+$ or $Mg^{++}$, or H; and
iii) mixtures thereof.

c) from about 0.1 to about 10% by weight of a stabilizer;
d) from about 5% to about 30% by weight of a lathering surfactant; and
e) water.

13. A liquid personal cleansing composition according to claim 12 wherein the complex coacervate particles comprise from about 0.1% to about 15% polycation having a minimum filtrate weight of about 10 grams and from about 0.01% to about 10% of a polyanion.

19. A liquid personal cleansing composition according to claim 18 wherein the viscosity of the liquid personal cleansing composition ranges from about 2,000 centipoise to about 100,000 centipoise and a yield point ranging from about 5 to about 90 dynes/sq. cm.

* * * * *

UNITED STATES PATENT AND TRADEMARK OFFICE
CERTIFICATE OF CORRECTION

PATENT NO. : 6,028,043      Page 1 of 1
APPLICATION NO. : 09/193539
DATED : February 22, 2000
INVENTOR(S) : R.W. Glenn, Jr. et al.

It is certified that error appears in the above-identified patent and that said Letters Patent is hereby corrected as shown below:

In Col. 16:
Claim 8, line 12 of the chemical structure, "[Alkyl]Alkylene" should read --Alkylene--.
In Col. 16:
Claim 8, line 13 of the chemical structure, "[Alkyl]Alkylene" should read --Alkylene--.
In Col. 16:
Claim 8, line 16 of the chemical structure, delete the text "[, provided $R_4$ and $R_5$ is H when not an alkyl group]".
In Col. 16:
Claim 8, line 22 of the chemical structure, delete the text
"[$R_7$ is — $R_4$ (COH)x$R_5$(COH)y$R_6$]".
In Col. 17:
line 25, "moisturizng" should read --moisturizing--.
In Col. 18:
Claim 18, line 6 of the chemical structure, add the text --wherein--.
In Col. 18:
Claim 18, line 12 of the chemical structure, "[Alkyl]Alkylene" should read --Alkylene--.
In Col. 18:
Claim 18, line 13 of the chemical structure, "[Alkyl]Alkylene" should read --Alkylene--.
In Col. 18:
Claim 18, line 16 of the chemical structure, delete the text "[, provided $R_4$ and $R_5$ is H when not an alkyl group]".
In Col. 18:
Claim 18, line 22 of the chemical structure, delete the text
"[$R_7$ is — $R_4$ (COH)x$R_5$(COH)y$R_6$]".

Signed and Sealed this

Thirty-first Day of July, 2007

JON W. DUDAS
*Director of the United States Patent and Trademark Office*